(12) United States Patent
Yoon et al.

(10) Patent No.: US 7,540,293 B2
(45) Date of Patent: Jun. 2, 2009

(54) DISHWASHER

(75) Inventors: Sang Heon Yoon, Seoul (KR); Nung Seo Park, Incheon (KR); Hung Myong Cho, Gimhae-si (KR); Dae Yeong Han, Seoul (KR)

(73) Assignee: LG Electronics Inc., Seoul (KR)

( * ) Notice: Subject to any disclaimer, the term of this patent is extended or adjusted under 35 U.S.C. 154(b) by 518 days.

(21) Appl. No.: 11/056,400

(22) Filed: Feb. 14, 2005

(65) Prior Publication Data

US 2006/0054196 A1   Mar. 16, 2006

(30) Foreign Application Priority Data

Sep. 14, 2004   (KR)   .................. 10-2004-0073400

(51) Int. Cl.
*B08B 3/02* (2006.01)
(52) U.S. Cl. .................................... 134/56 D; 134/113
(58) Field of Classification Search ................ 134/113, 134/184, 198; 68/12.02
See application file for complete search history.

(56) References Cited

U.S. PATENT DOCUMENTS

| | | | | |
|---|---|---|---|---|
| 3,613,405 A | * | 10/1971 | Shimokusu | ................ 68/12.02 |
| 3,807,418 A | * | 4/1974 | Jenkins | ..................... 134/57 D |
| 3,870,417 A | * | 3/1975 | Bashark | ...................... 356/442 |
| 4,559,959 A | * | 12/1985 | Meyers | ..................... 134/56 D |
| 4,653,294 A | * | 3/1987 | Akinaga | .................... 68/12.21 |
| 5,165,433 A | | 11/1992 | Meyers | |
| 5,429,146 A | * | 7/1995 | Graf et al. | ................. 134/58 D |
| 5,446,531 A | * | 8/1995 | Boyer et al. | ................... 356/72 |
| 6,456,375 B1 | * | 9/2002 | Ottens et al. | ................ 356/339 |
| 2003/0019510 A1 | | 1/2003 | Hegeman et al. | |
| 2003/0213503 A1 | * | 11/2003 | Price et al. | ..................... 134/18 |

FOREIGN PATENT DOCUMENTS

| | | | |
|---|---|---|---|
| EP | 1 180 344 A2 | | 2/2002 |
| JP | 4-240485 | * | 8/1992 |
| JP | 6-22897 | * | 2/1994 |
| JP | 6-285286 | * | 10/1994 |
| KR | 10-1998-041194 | | 8/1998 |
| KR | 1998-036847 | | 8/1998 |

* cited by examiner

*Primary Examiner*—Frankie L Stinson
(74) *Attorney, Agent, or Firm*—McKenna Long & Aldridge LLP

(57) ABSTRACT

A dishwasher is disclosed, including a sump for receiving wash water for washing contaminated dishes; a main motor for circulating wash water in the sump; a washing pump connected with the main motor and pumping the wash water; a main channel and a sampling channel formed in a drain direction of the washing pump; and a contamination sensor mounted at a channel extension part located at the sampling channel and measuring contamination of the wash water. The dishwasher of the present invention is able to measure contamination of wash water for washing dishes and to mount the contamination sensor for measuring the contamination of the wash water with ease.

9 Claims, 7 Drawing Sheets

DISHWASHER

CROSS-REFERENCE TO RELATED APPLICATIONS

This application claims the benefit of Korean Application No. P2004-73400, filed on Sep. 14, 2004, which is hereby incorporated by reference as if fully set forth herein.

BACKGROUND OF THE INVENTION

1. Field of the Invention

The present invention relates to a dishwasher, and more particularly, to a dishwasher with an improved structure for exactly estimating a pollution level of wash water.

2. Discussion of the Related Art

In general, a dishwasher is an apparatus for automatically washing dishes. Owing to the functions of washing, rinsing, drying, and storing dishes, the dishwasher greatly reduces housework.

A washing method of the dishwasher is divided into a shower type and a supersonic type. The shower type dishwasher is normally employed for domestic use. The shower type dishwasher washes dishes by spraying hot water on dishes put in a dish basket, the water in which detergent dissolved. A method for spraying water includes spraying using a propeller, and boring a plurality of holes on a pipe and rotating the pipe.

Referring to FIG. 1, structural elements of a conventional dishwasher will be briefly described as follows. The conventional dishwasher includes a water collection part 1, a motor 2 for driving the water collection part 1, and upper and lower washing parts 3 and 4 through which wash water flowed in from the water collection part is sprayed.

The water collection part 1 is provided with a main water collection part 1a for receiving water from outside, or collecting and discharging polluted water after washing. A channel forming part 1b having a channel formed thereat for moving wash water to upper and lower washing part is provided at an upper part of the main water collection part 1a, the wash water circulating in the dishwasher. A filtering part 1c for removing contaminants by filtering the wash water is connected to the channel forming part 1b.

The motor 2 drives a washing pump for supplying wash water to upper and lower parts 3 and 4 during dishwashing, or provides power for driving a drain pump. The upper and lower washing parts 3 and 4 are places wherein dishwashing is actually performed, and connected to the water collection part through a coupling pipe. A spraying arm (not shown) washes contaminated dishes by spraying wash water supplied from the water collection part 1.

Operation process of the conventional dishwasher will be sequentially described as follows. First, dishes to be washed are put in the dish basket, and an administration is inputted. Then, a predetermined amount of wash water is filled in the main water collection part of the dishwasher through a supply valve connected with the outside of the dishwasher.

Thereafter, the dishwasher heats the supplied wash water by driving a heater, and drives a washing pump by driving a motor. Then, the heated wash water is moved to upper and lower spraying arm through a coupling pipe via the washing pump. The wash water reached to the spraying arm is sprayed through a spraying nozzle so as to remove contaminants on surfaces of the dishes.

After dishwashing, the contaminants and the wash water separated from the dishes are collected at the main water collection part. When the contamination of the wash water is over a predetermined level, the dishwasher discharges wash water mixed with contaminants and is supplied with fresh water from the outside.

When the contamination of the wash water is under the predetermined level, the dishwasher purifies the wash water collected at the water collection part and moves the refreshed water back to the upper and lower parts of the spraying arm via the washing pump. When the washing is terminated, the wash water collected in the main collection part is discharged to the outside through the drain pump, along with the contaminants.

Meanwhile, in the conventional dishwasher, a three-way valve is employed for controlling the direction of the wash water, and normally a solenoid valve is employed. The solenoid valve is automatically opened and closed by the principle of electromagnetic induction, and usually employed for automation of machines or to a safety device.

The conventional dishwasher however has problems as follows. First, in the conventional dishwasher, a channel for measuring contamination of wash water is not separately provided, and the contamination of the wash water is measured on the channel through which the wash water flows to a spraying arm. Accordingly, since a contamination sensor of the conventional dishwasher measures contamination of the wash water flowing at a high speed, there is a problem that the contamination level of the wash water may be inaccurate.

Second, since a channel through which a large amount of wash water passes is formed at the conventional contamination sensor, the size of the contamination sensor itself becomes large, and thus mounting the contamination sensor is complicated.

SUMMARY OF THE INVENTION

Accordingly, the present invention is directed to a dishwasher that substantially obviates one or more problems due to limitations and disadvantages of the related art.

An object of the present invention is to provide a dishwasher for accurately measuring contamination of wash water.

Another object of the present invention is to provide a dishwasher enabling mounting a contamination sensor with ease, the contamination sensor for measuring contamination level of wash water.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a dishwasher includes a sump for receiving wash water for washing contaminated dishes, a main motor for circulating wash water in the sump, a washing pump connected with the main motor and pumping the wash water, a main channel and a sampling channel formed in a drain direction of the washing pump, and a contamination sensor mounted at a channel extension part located at the sampling channel and measuring contamination of the wash water.

Desirably, the sampling channel is formed at an upper housing mounted at an upper part of the sump and has a width smaller than that of the main channel.

The sampling channel includes a first side connected with an inflow channel, and a second side connected with a drain pump for discharging the wash water.

The contamination sensor includes a measuring element for measuring contamination of the wash water, a measuring element housing surrounding the measuring element, and a housing coupling part formed at a side of the measuring element housing.

Desirably, the measuring element housing includes a measuring channel through which the wash water is flown. The measuring channel is at a predetermined angle to the sampling channel.

An upper end surface of the contamination sensor is lower that the height of the sampling channel when the contamination sensor is mounted at the channel extension part.

Desirably, a sensor mounting part is protruded from a floor surface of the outside of the sump and includes an insertion hole having the contamination sensor passing therethrough. Desirably, a length of the protruded sensor mounting part is shorter that a total length of the contamination sensor.

Desirably, a coupling projection is formed at a predetermined location of the sensor mounting part, and the coupling projection corresponds to a coupling hole formed at the housing coupling part.

Desirably, the housing coupling part is made of an elastic member, and the sensor mounting part and the housing coupling member are screw-coupled to each other.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
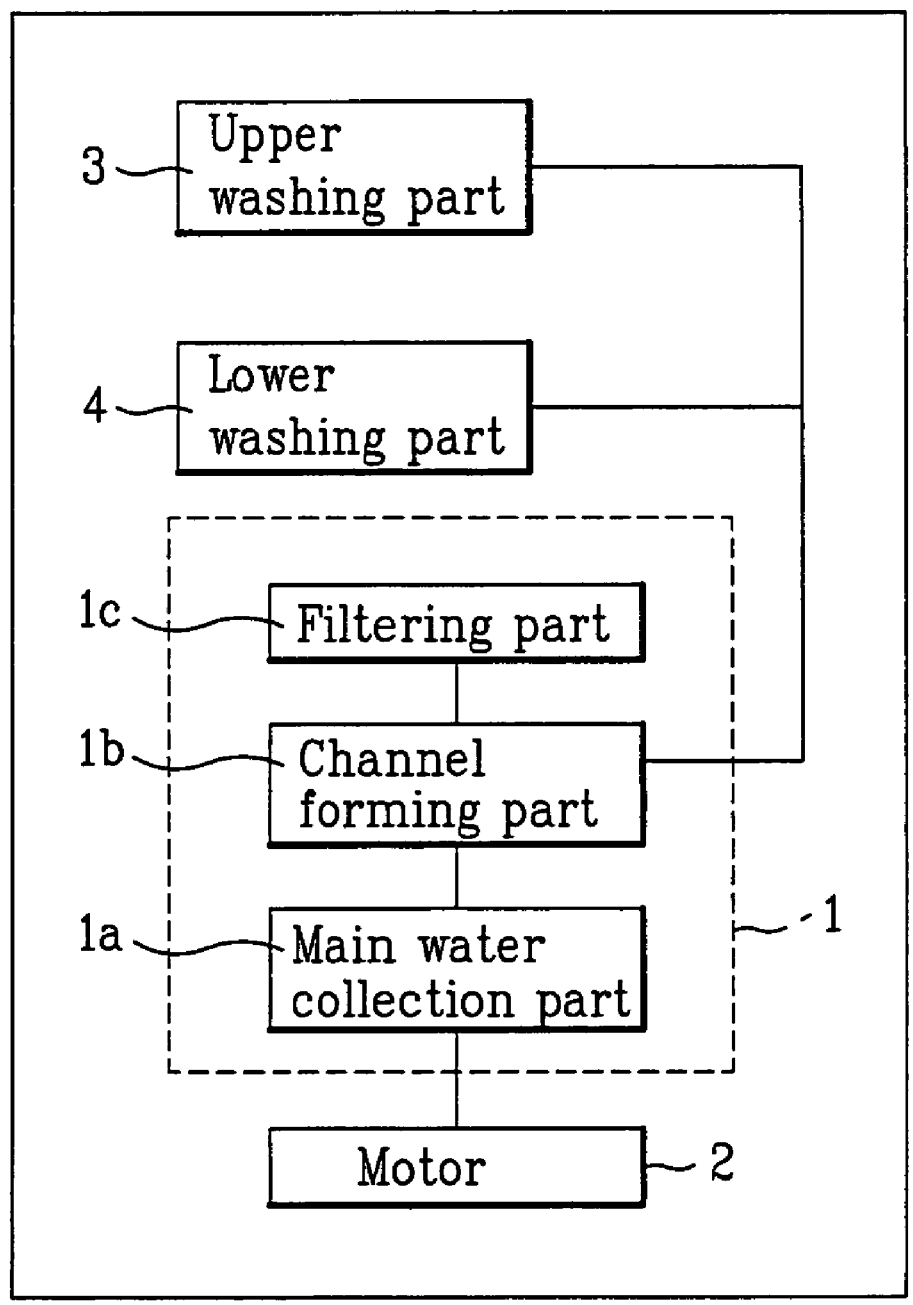
FIG. 1 illustrates a block diagram showing an inner structure of a conventional dishwasher.
Figure 2:
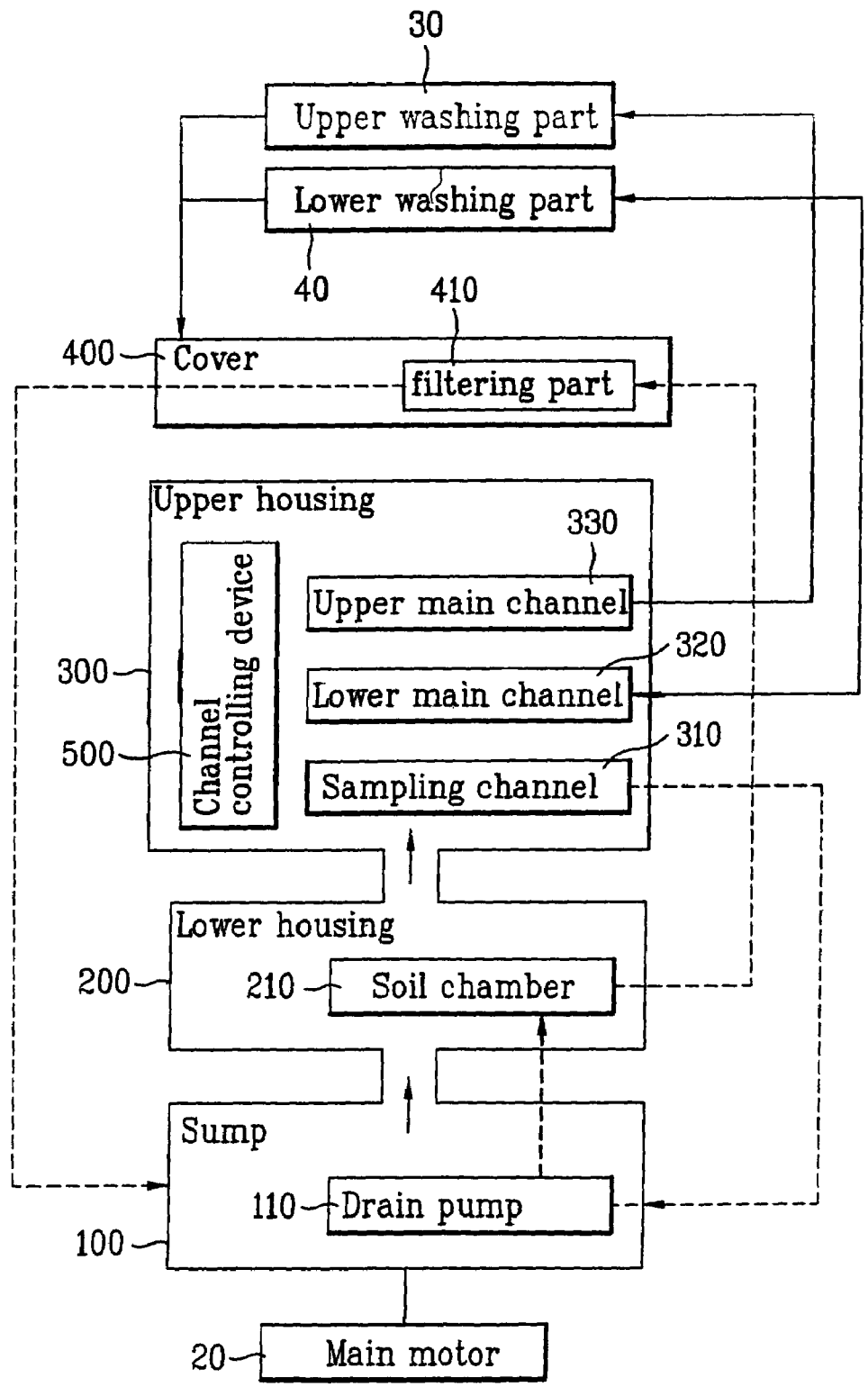
FIG. 2 illustrates a block diagram showing an inner structure of a first embodiment of the dishwasher in accordance with the present invention.

With reference to FIG. 2, a channel through which the wash water of a dishwasher in accordance with the present invention will be briefly described as follows.

A sump 100 is mounted at a lower end of the dishwasher, and a lower housing 200 having a soil chamber 210 formed thereat is mounted at an upper part of the sump 100. An upper housing 300 having a channel of the wash water is mounted at an upper part of the lower housing 200, and a cover 400 for covering the upper housing is mounted at an upper part of the upper housing 300.

First, the wash water in the sump 100 is moved through the lower housing 200 to the upper housing 300 via a washing pump. Then, via a channel controlling device 500, the wash water is moved to an upper washing arm through an upper main channel 330 formed at the upper housing 300, and to a lower washing arm through a lower main channel 320.

A part of the wash water is moved to a drain pump 110 through a sampling channel 310. The wash water passed through the drain pump 110 is flowed into the soil chamber 210 of the lower housing 200, and filtered at a filtering part 410 formed at the cover 400. The wash water filtered at the filtering part 410 is collected at the sump 100.

Contrary to the dishwasher of the related art, the present embodiment mentioned above has a sampling channel 310 for measurement and filtering of contamination.

Since the sampling channel 310 is connected with the soil chamber 210 through the washing pump and the drain pump 110, pressure on the filtering part 410 is lowered by the washing pump. Accordingly, the filtering part 410 formed at the cover 400 is rarely closed by contaminants.

Figure 3:
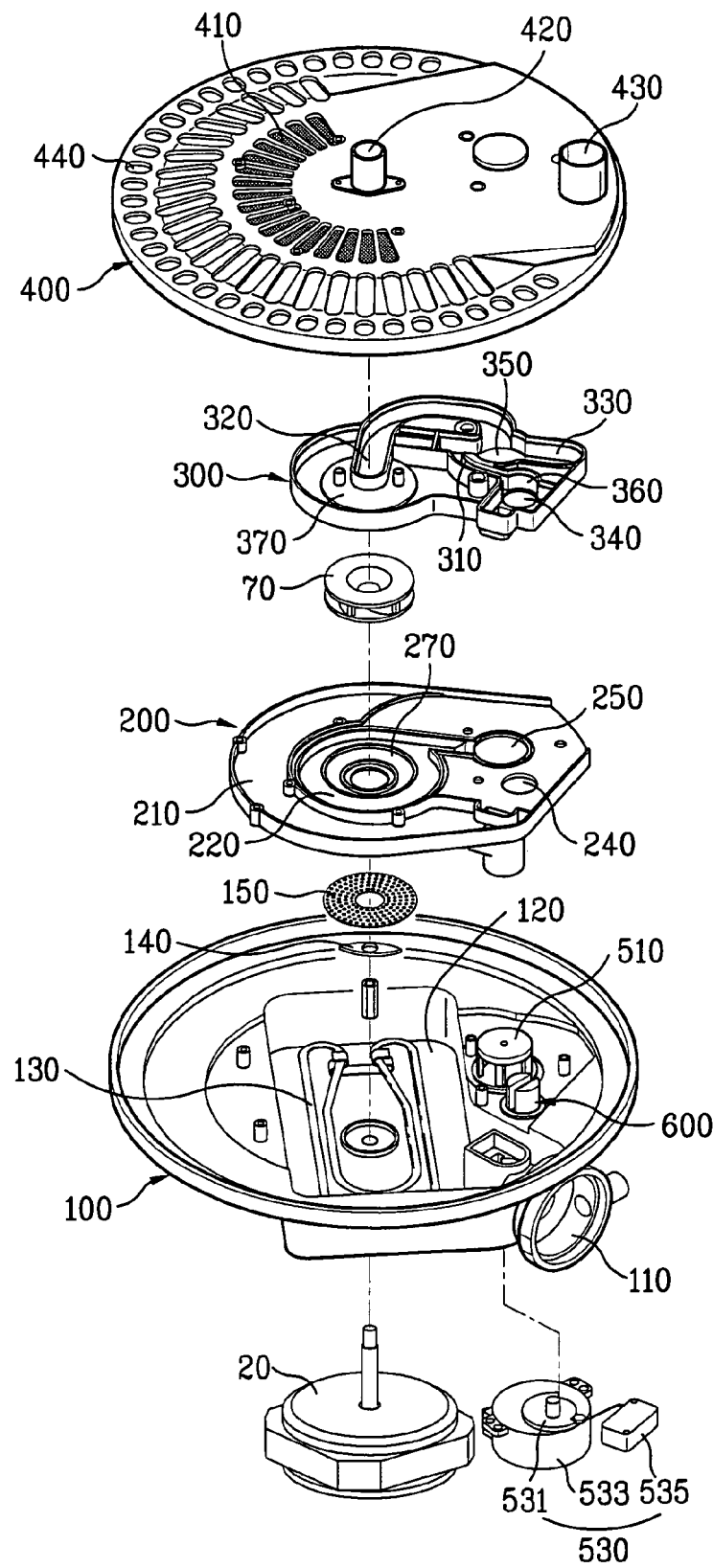
FIG. 3 illustrates a schematic perspective view showing important structural elements of FIG. 2.

Referring to FIG. 3, a structure of a water collection device in the dishwasher in accordance with FIG. 2 will be described.

A main motor 20 for providing a driving force to the dishwasher is mounted at a lower end of the water collection device, and a sump 100 having a wash water receiving part 120 for collecting wash water is mounted at an upper part of the main motor 20.

The lower housing 200 having the soil chamber 210 formed thereat is mounted at an upper part of the sump 100, and the upper housing 300 having a channel through which the wash water is flowed is mounted at the lower housing 200. The cover 400 for filtering the wash water and returning the wash water to the sump 100 is mounted at an upper part of the upper housing 300.

A heater 130 is mounted in the sump 100, and it is desirable that the heater 130 always be remained under the wash water during the operation of the dishwasher. The heater 130 performs a role of making it easy to wash the dishes by heating the wash water at a proper temperature.

A valve controller 530 for controlling a channel control valve and main motor 20 are mounted on an outer floor surface of the sump 100, and a drain pump 110 is mounted on an outer lateral surface. The main motor and the valve controller in the present invention may be mounted on an outer lateral surface of the sump, and the drain pump may be mounted on the outer floor surface of the sump.

The lower housing 200 includes a first pass through hole 240 having a contamination sensor 600 passed therethrough for measuring contamination of the wash water, and a soil chamber 210 for collecting the wash water passed through the contamination sensor 600 and the drain pump 110.

An impeller accommodator 270 for accommodating an impeller 70 is formed at the center of the lower housing 200, and an inflow channel 220 is formed at the outside of the impeller accommodator 270, the inflow channel 220 through which the wash water moved by the impeller is flowed into the channel control valve 510. A second pass through hole 250 through which the channel control valve 510 is passed is formed at a part connected with the inflow channel 220.

An impeller cap 370 for accommodating the upper part of the impeller 70 and a second pass through hole 350 through which the channel control valve 510 are formed at the upper housing 300. In addition, an upper main channel 330 connected with the second pass through hole 350 and sending the wash water to an upper washing arm, a lower main channel 320 for sending wash water to the lower washing arm, and a sampling channel 310 for sending wash water to the drain pump 110 are further formed.

A channel extension part 360 having the contamination sensor 600 mounted thereat is formed on the sampling channel, and a first pass through hole 340 through which the contamination sensor is passed is formed in the center of the channel extension part. Although it is desirable that the upper housing and the lower housing be separately provided, the upper housing and the lower housing may be formed as a single body.

The impeller 70 is mounted between the upper housing 300 and the lower housing 200, and axially coupled with the main motor 20. The impeller 70 is rotated by the main motor 20, and, due to the rotation motion, wash water is flowed into the inflow channel 220 from the wash water accommodating part 120 of the sump 100.

The wash water passed through the inflow channel 220 is divided into the aforementioned upper main channel 330, the lower main channel 320, and the sampling channel 310 via a channel controlling device. The channel controlling device includes a channel control valve 510 for controlling the direction of the wash water, a valve controller 530 for controlling the channel control valve 510, and a packing member (not shown) mounted between the channel control valve and the valve controller. The channel control valve 510 and the packing member are mounted in a sump, and the valve controller 530 is mounted at an outer lower end of the sump.

The cover 400 includes a filtering part 410 mounted in the center of the cover 400, and a return hole 440 formed in a predetermined shape at an edge of the cover 400. The return hole 440 is formed for returning the wash water to the sump 100, the wash water filtered by the filtering part 410.

The cover 400 includes an upper arm coupling part 430 performing a role of a passage through which the wash water is passed from the main channel to an upper spraying arm, and a lower arm coupling part 420 performing a role of a passage through which the wash water is passed from the lower main channel to a lower spraying arm. The cover 400 and the upper housing 300 may be integrated into a single body via heat fusion, or may be separately mounted and then coupled via a coupling means.

Figure 4:
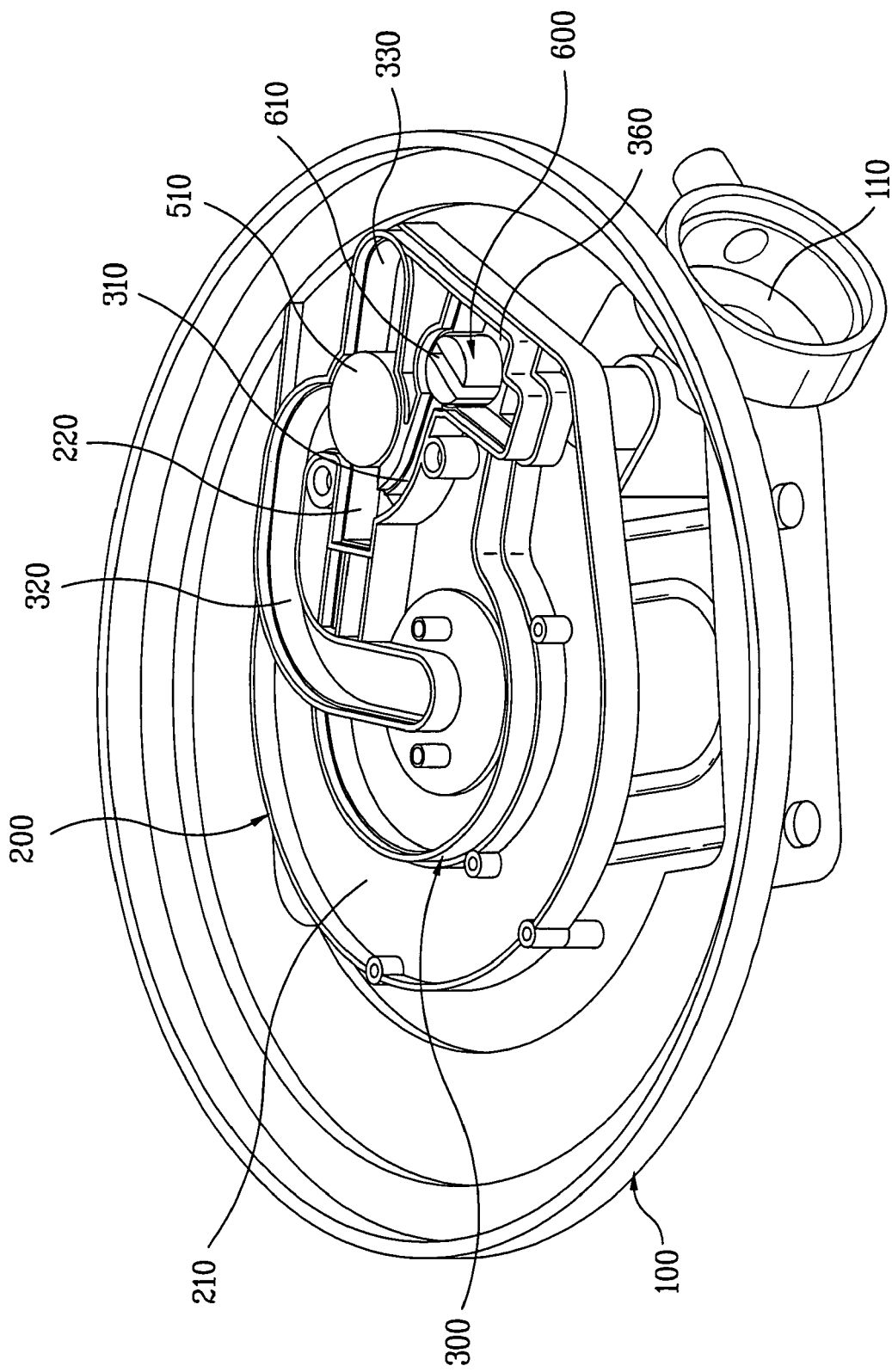
FIG. 4 illustrates a perspective view showing a state that a contamination sensor of FIG. 3 is provided.

Referring to FIG. 4, the position of the contamination sensor mounted in the sump, and the structure thereof will be concretely described. As mentioned above, the lower housing 200 having the soil chamber 210 formed thereat is mounted at an upper part of the sump 100, and an upper main channel 330, a lower main channel 320, and a sampling channel 310 are mounted at an upper part of the lower housing 200. In addition, a contamination sensor 600 for measuring the contamination level of the wash water is mounted on the sampling channel 310.

The sampling channel 310 includes a first side connected with an inflow channel 220 through which the wash water is flowed into the upper housing 300, and a second side connected with the drain pump 110. The sampling channel 310 is formed to have a smaller width than widths of the upper main channel 330 and the lower main channel 320.

The contamination sensor 600 passes through a first pass through hole (240) formed at the lower housing 200, and a first pass through hole (340) formed at the upper housing 300, and then mounted on the sampling channel 310.

In more detail, the contamination sensor 600 is mounted at a channel extension part 360 for extending the sampling channel 310. It is desirable that the channel extension part 360 be formed at a coupling part between the upper housing 300 and the drain pump 110.

It is desirable that an upper section of the contamination sensor 600 be mounted to be lower than the height of the sampling channel, that is, the upper section of the upper housing 300 so as to enlarge the channel extension part 360. Accordingly, the velocity of the water is lowered when the wash water is flowed into the channel extension part 360 and thus the contamination of the wash water can be measured exactly.

A measuring channel 610 formed at the contamination sensor 600 is mounted at a predetermined angle from the sampling channel 310. In more detail, it is desirable that the sampling channel 310 and the measuring channel 610 be vertically mounted because the velocity of wash water is higher when the sampling channel 310 and the measuring channel 610 are connected in a straight line than when the sampling channel 310 and the measuring channel 610 are mounted at a predetermined angle.

Figure 5:
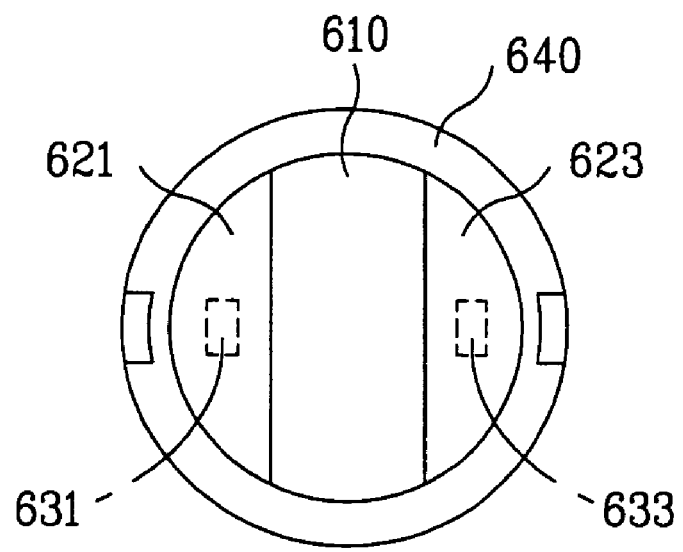
FIG. 5 illustrates a front view and a rear view of a first embodiment of a contamination sensor in accordance with the present invention.
Figure 5:
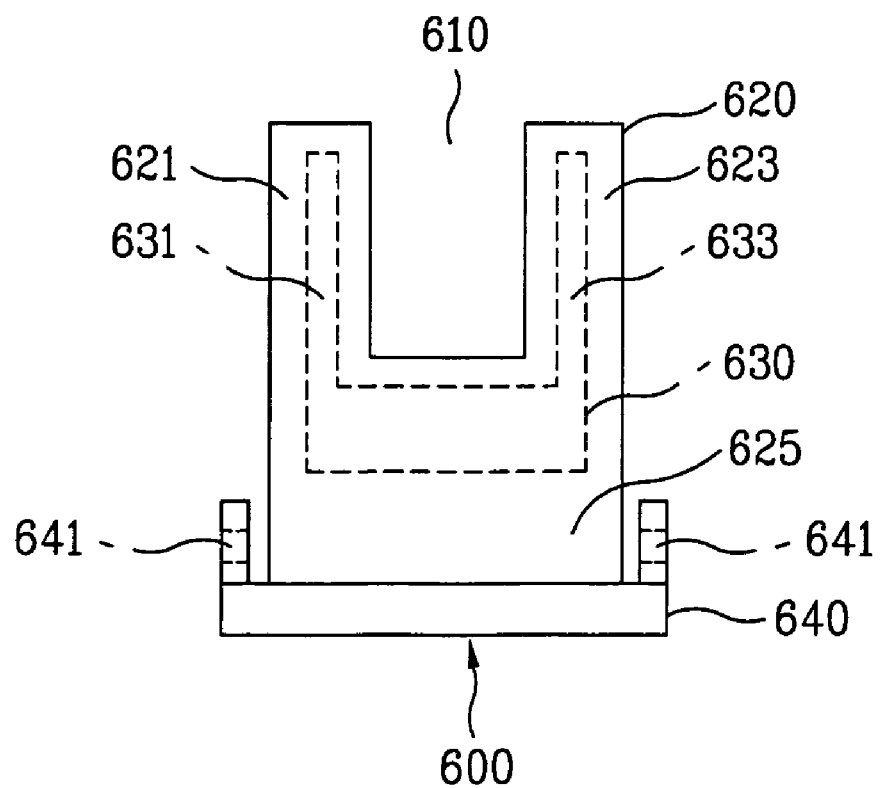

Referring to FIG. 5, a first embodiment of the contamination sensor in accordance with the present invention will be described. The contamination sensor 600 includes a measuring element 630 for measuring contamination of wash water, a measuring element housing 620 surrounding the measuring element, and a housing coupling part 640 formed at a side of the measuring element housing.

The measuring element 630 includes a light emitting element 631 for emitting a laser beam, and a light receiving element 633 for receiving the beam emitted from the light emitting element 631.

The emitting element 631 is spaced for a predetermined distance from the light receiving element 633, and wash water is flowed between the light emitting element 631 and the light receiving element 633.

The light emitting element 631 emits beams to the flowing wash water, and the light receiving element 633 receives the emitted beams. At this time, the contamination level of the wash water is measured by interaction of the received beams.

The measuring element housing 620 includes a light receiving housing 623 surrounding the light receiving element, a light emitting housing 621, and a base part 625 for supporting the light receiving housing and the light emitting housing.

A measuring channel 610 through which the wash water is flowed is formed between the light receiving housing 623 and the light emitting housing 621, and the measuring channel 610 is connected with the sampling channel 310 formed at the upper housing.

The housing coupling part 640 is formed at a side of the measuring element housing 620, and performs a role of coupling the contamination sensor 600 to a sump. The housing coupling part 640 includes a coupling hole 641 formed in a predetermined shape corresponding to a coupling projection formed outside of the lower part of the sump. It is desirable that the housing coupling part 640 be made of an elastic member, and include at least one coupling hole 641.

Figure 6:
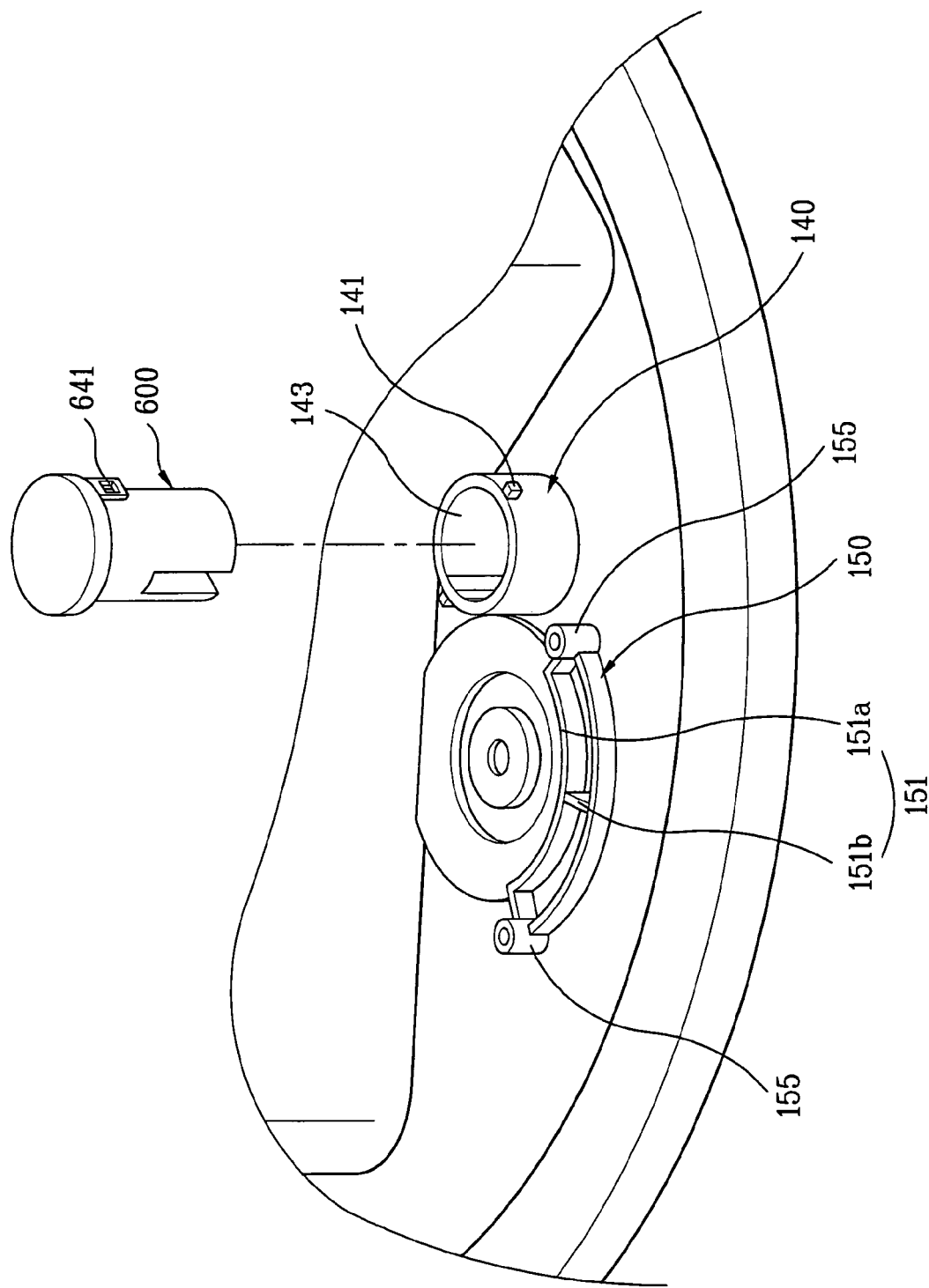
FIG. 6 illustrates a schematic view showing a state that the contamination sensor of FIG. 5 is coupled.

Referring to FIG. 6, the structure of the contamination sensor coupled with the outside of the lower part of the sump will be concretely described. A motor mounting part 150 for driving a channel control valve (not shown) and a sensor mounting part 140 having the contamination sensor 600 mounted thereat are neighboring to the outside of the sump.

The sensor mounting part 140 is protruded from a floor surface on the outside of the sump 100, and an insertion hole 143 through which the contamination sensor 600 is inserted is formed in the sensor mounting part.

In more detail, the sensor mounting part 140 is formed in a cylinder shape and having a predetermined length with opened both sides, and the length of the sensor mounting part is sorter than the total length of the contamination sensor 600.

The shape of the sensor mounting part may be formed in an arbitrary shape, if the shape is corresponding to the contamination sensor. For example, if the contamination sensor is a rectangular parallelepiped, the shape of the coupling part has a square cylinder.

Meanwhile, a coupling projection 141 formed in a predetermined shape is formed at an outer circumference of the sensor mounting part 140, and the coupling projection 141 corresponds to a coupling hole 641 formed at the housing coupling part of the contamination sensor.

At least one coupling projection 141 is formed at the outer circumference of the sensor mounting part, and the shape of the coupling projection 141 may be formed in any shape, only if the shape corresponds to the coupling hole.

The motor mounting part 150 is cut at a predetermined angle and formed in a ring shape. The motor mounting part 150 includes a supplementary rib 151 for increasing the strength of the outside of the sump and easily coupling with a valve motor, and a motor coupling boss 155 for coupling the valve motor with the sump.

The supplementary rib 151 is includes a circumferential rib 151a forming the circumference of the motor mounting part, having a predetermined width and protruded to the outside of the sump, and a middle rib 151b connecting the circumference rib. It is desirable that at least one middle rib 151b be formed.

The motor coupling boss 155 is formed at a predetermined location of the supplementary rib 151, and a thread is formed at the motor coupling boss 155. In addition, it is desirable that at least one motor coupling boss 155 is formed.

Figure 7:
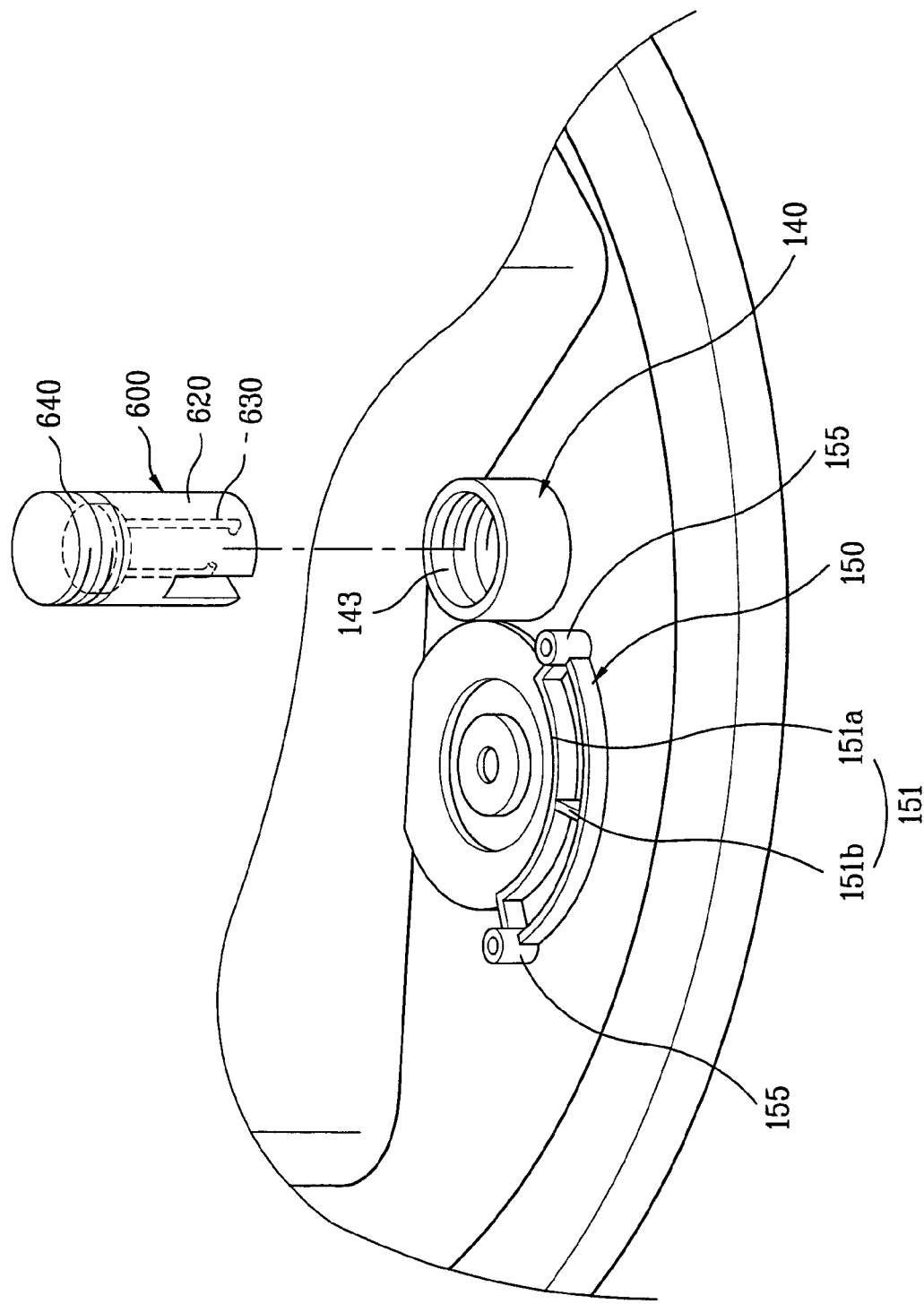
FIG. 7 illustrates a schematic view showing a state that a second embodiment of the contamination sensor in accordance with the present invention is coupled.

Referring to FIG. 7, a second embodiment of the contamination sensor in accordance with the present invention will be described. In the same manner as the first embodiment mentioned above, the contamination sensor 600 includes a measuring element 630 for measuring contamination of wash water, a measuring element housing 620 surrounding the measuring element, and a housing coupling part 640 formed at a side of the measuring element housing. The contamination sensor 600 is coupled with a sensor mounting part 140 formed at the outside of the lower part of the sump.

Contrary to the first embodiment mentioned above, the housing coupling part 640 includes a male screw at the circumference of the housing coupling part, and a female screw formed in the sensor mounting part 140. The housing coupling part may be coupled with the coupling part of the measuring sensor in various coupling methods including a method of inserting coupling the housing coupling part into the coupling part of the measuring sensor.

Effects of the dishwasher in accordance with the present invention will be described as follows. First, in the dishwasher in accordance with the present invention, the contamination of the wash water is more accurately measured by separately forming a sampling channel and mounting a contamination sensor at a channel extension part of the sampling channel. Second, the contamination sensor is mounted with ease by using a proper contamination sensor fitting in the width of the sampling channel in accordance with the present invention and reducing the size of the contamination sensor. Third, the contamination sensor in accordance with the present invention has a simple coupling structure and thus is easy to use.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A dishwasher comprising:
   a sump for receiving wash water for washing contaminated dishes;
   a main motor for circulating wash water in the sump;
   a washing pump connected with the main motor and pumping the wash water;
   a main channel and a sampling channel formed in a drain direction of the washing pump; and
   a contamination sensor mounted at a channel extension part located at the sampling channel and measuring contamination level of the wash water, wherein the contamination sensor protrudes from a surface of the sump;
   wherein the sampling channel is formed at an upper housing mounted at an upper part of the sump and has a width smaller than that of the main channel; and
   wherein the contamination sensor comprises:
   a measuring element for measuring contamination of the wash water;
   a measuring element housing surrounding the measuring element; and
   a housing coupling part formed at a side of the measuring element housing.

2. The dishwasher of claim 1, wherein the measuring element housing comprises a measuring channel through which the wash water is flown.

3. The dishwasher of claim 2, wherein the measuring channel is at a predetermined angle to the sampling channel.

4. The dishwasher of claim 1, wherein an upper end surface of the contamination sensor is lower that the height of the sampling channel when the contamination sensor is mounted at the channel extension part.

5. The dishwasher of claim 1, wherein a sensor mounting part is protruded from a floor surface of the outside of the sump and comprises an insertion hole having the contamination sensor passing therethrough.

6. The dishwasher of claim 5, wherein a length of the protruded sensor mounting part is shorter that a total length of the contamination sensor.

7. The dishwasher of claim 5, wherein a coupling projection is formed at a predetermined location of the sensor mounting part, and the coupling projection corresponds to a coupling hole formed at the housing coupling part.

8. The dishwasher of claim 7, wherein the housing coupling part is made of an elastic member.

9. The dishwasher of claim 5, wherein the sensor mounting part and the housing coupling member are screw-coupled to each other.

\* \* \* \* \*